(12) United States Patent
Madsen et al.

(10) Patent No.: US 6,642,215 B2
(45) Date of Patent: Nov. 4, 2003

(54) METHOD OF MODULATING NF-KB ACTIVITY

(75) Inventors: Mogens Winkel Madsen, Virum (DK); Lone Stengelshøj Olsen, Glostrup (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 10/153,800

(22) Filed: May 24, 2002

(65) Prior Publication Data

US 2003/0004192 A1 Jan. 2, 2003

Related U.S. Application Data

(60) Provisional application No. 60/292,927, filed on May 24, 2001.

(51) Int. Cl.[7] .............................................. A61K 31/675
(52) U.S. Cl. ....................... 514/89; 514/344; 514/346; 514/352
(58) Field of Search ................................ 514/352, 344, 514/346, 89

(56) References Cited

U.S. PATENT DOCUMENTS 6,121,297 A * 9/2000 Ottosen ....................... 514/352

FOREIGN PATENT DOCUMENTS

| WO | WO 98/08955 | | 3/1998 | |
|----|----|----|----|----|
| WO | 98/37228 | * | 8/1998 | ................. 514/352 |
| WO | WO 98/54142 | | 12/1998 | |
| WO | WO 98/54143 | | 12/1998 | |
| WO | 00/61561 | * | 10/2000 | ................. 514/352 |
| WO | 00/61559 | * | 12/2000 | ................. 514/352 |
| WO | 00/76516 | * | 12/2000 | ................. 514/352 |
| WO | 00/76517 | * | 12/2000 | ................. 514/352 |

OTHER PUBLICATIONS

Ekelund et al., Biochemical Pharmacology, vol. 61 (2001) pp. 1183–1193.
Vig Hjarnaa et al., Cancer Research, vol. 59 (1999) pp. 5751–5757.
Martinsson et al., European Journal of Pharmacology, vol. 417 (2001) pp. 181–187.
Schou et al., Bioorganic & Medicinal Chemistry Letters, vol. 7, No. 24 (1997) pp. 3095–3100.
Svensson et al., Pediatric Research, vol. 51, No. 5 (2002) pp. 607–611.

XP008007249 abstract, #5297 Elucidation of possible mechanisms of action of the novel pyridyl cyanoguanidine anticancer agent CHS828 in a resistant human small cell lung cancer line NYH/CHS, Proceedings of the American Association for Cancer Research Annual, No. 41, Mar. 2000, p. 834.

* cited by examiner

*Primary Examiner*—James H Reamer
(74) *Attorney, Agent, or Firm*—Birch, Stewart, Kolasch & Birch, LLP

(57) ABSTRACT

A method of modulating the level of activated, NF-κB in cells by contacting cells with a cyanoguanidine compound of general formula I

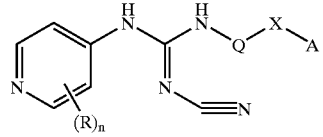

[I]

wherein n is 0, 1 or 2;

each R independently represents halogen, trifluoromethyl, hydroxy, $C_{1-4}$ alkyl, $C_{1-4}$ alkoxy, $C_{1-4}$ alkoxycarbonyl, nitro, cyano, amino, sulfo or carboxy groups;

Q is a straight or branched, saturated or unsaturated $C_{4-20}$ divalent hydrocarbon radical;

X is a bond, O, S, amino, carbonyl, carbonylamino, aminocarbonyl, oxycarbonyloxy, oxycarbonyl, carbonyloxy, aminocarbonyloxy, aminothiocarbonyloxy, oxycarbonylamino or oxythiocarbonylamino;

A is di-($C_{1-4}$ alkoxy)phosphinoyloxy, $C_{1-4}$ alkoxycarbonyl, $C_{1-4}$ alkoxycarbonylamino, saturated or unsaturated $C_{3-12}$ carbocyclic ring or $C_{3-12}$ heterocarbocyclic ring optionally substituted with one or more $R_1$; $R_1$ being independently selected from the group consisting of halogen, trifluoromethyl, hydroxy, $C_{1-4}$ alkyl, $C_{1-4}$ alkoxy, $C_{1-4}$ alkoxycarbonyl, nitro, cyano, amino, carboxy, sulfo, carboxamido, sulfamoyl or $C_{1-4}$ hydroxyalkyl;

or a pharmaceutically acceptable salt, N-oxide or N-substituted prodrug thereof, in an amount effective to modulate the activity of IKK.

38 Claims, 5 Drawing Sheets

METHOD OF MODULATING NF-κB ACTIVITY

This application claims priority on provisional Application No. 60/292,927 filed on May 24, 2001, the entire contents of which are hereby incorporated by reference.

FIELD OF INVENTION

The present invention relates to methods of modulating the activity of NF-κB and to methods of inhibiting the IκB complex (IKK) using cyanoguanidine derivatives.

BACKGROUND OF THE INVENTION

Neoplastic diseases are characterised by autonomous growth of cells. Neoplastic diseases may be benign, i.e. the growth is contained and does not spread to other organs or parts of the body. Neoplastic diseases may also be malignant where the growth spreads to other organs or parts of the body by infiltration or metastases. Malignant neoplastic diseases are also known as cancers.

Patients with neoplastic diseases are treated by surgery, ionising radiation, medication, or a combination thereof. Several types of medicaments or drugs for the treatment of neoplastic diseases are known, and one way of classifying these medicaments is suggested in Abeloff et al (Eds.), *Clinical Oncology,* Churchill Livingston Inc., New York, 1995, Medicaments for treatment of neoplastic diseases may conveniently by classified as chemotherapeutic agents, hormonal agents or biological response modifiers.

Chemotherapeutic agents may further be classified according to the mechanism whereby they effect their response as S-triazine derivatives such as altretamine; as enzymes such as asparaginase; as antibiotic agents such as bleomycin, dactinomycin, daunorubicin, doxorubicin, idarubicin, mitomycin and plicamycin; as alkylating agents such as busulfan, carboplatin, carmustine, chlorambucil, cisplatin, cyclophosphamid, dacarbazine, ifosfamide, lomustine, mechlorethamine, melphalan, procarbazine and thiotepa; as antimetabolites such as cladribine, cytarabine, floxuridine, fludarabine, fluoruracil, hydroxyurea, mercaptopurine, methotrexate, pentostatin and thioguanine, and as antimitotic agents such as etoposide, paclitaxel, teniposide, vinblastine and vincristine.

Hormonal agents may be further classified according to the mechanism whereby they effect their response, e.g. as aromatase inhibitors such as aminoglutethimide; as antiestrogens such as tamoxifen, formestan and letrozol; and as antiandrogen such as flutamide.

Biological response modifiers may be further classified according to the mechanism whereby they effect their response as e.g. lymphokines such as aldesleukin; as interferon such as interferon-α and as growth factors such as erythropoietin, filgrastim and sagramostim.

A number of medicaments do not fall naturally within this classification. Examples of such medicaments are antiproliferative and/or cell differentiating agents such as all-trans retenoic acid or vitamin D analogues such as seocalcitol.

Other types of medicaments based on e.g monoclonal antibodies, tumour necrosis factor, gene therapy and angiogenisis inhibitors have been suggested for treatment of neoplastic diseases, but they are still in the exploratory phase.

Unfortunately, neoplastic cells are very effective in developing biochemical mechanisms that allow cellular resistance to medicaments or ionising radiation. In fact, resistance is a common clinical problem in the therapy of neoplastic diseases [Cun-Yu Wang, Nature Medicine, 5, 412–417, 1999]. In order to overcome this resistance, therapy generally involves more than one medicament or combinations of ionising radiation and medicaments. Several types of resistance are known, e.g. enhanced drug metabolism, altered drug accumulation, drug target amplification and repair of damaged targets. Resistance to apoptosis is another type of multi-drug resistance, that likely explains a significant proportion of treatment failures [Fisher, *Cell,* 78, 539–542, 1994]. For convenience, the terms "medicament" and "drug" are used interchangeably, and are intended to indicate the same.

Clearly, there is a need for new and improved methods in the treatment of neoplastic diseases. Direct manipulation of the factors controlling apoptosis (programmed cell death) is a more recently suggested approach to therapy of neoplastic diseases. Apoptosis is a genetically encoded cell death programme characterised by an "active decision" by the cell based on information from its environment, its own internal metabolism, its developmental history, etc to die. Unlike cells undergoing necrosis, cells stimulated to enter apoptosis are often capable of survival, but opt to die for the good of the whole organism. Apoptosis is also different from necrosis in that necrosis is often associated with traumatised tissue and cell bursts, whereas the cells condense in the course of apoptosis, and are degraded intracellularly in a controlled manner [Tran, *Science and Medicine,* 6, 18–27, 1999; Williams, *Trends Cell Biol.,* 2, 263–267, 1992].

At the cellular level it is well recognised that nuclear factor κB (NF-κB) plays a pivotal role in apoptosis. It is also described that an NF-κB inhibitor, IκB, and an IκB kinase complex, IKK, control the level of activated NFκB [Levkau, 1, 227–233, 1999; Wang, *Science,* 274, 784–787, 196; Madrid, *Molecular and Cellular Biology,* 5, 1626–1638, 2000]. Accordingly, the NF-κB-IκB-IKK system has been suggested as a target in the treatment of neoplastic diseases.

Cusack, *Cancer Research,* 60, 2323–2330, 2000 and Wang, *Nature Medicine* 5, 412–417, 1999 teach that a particular chemotherapeutic, namely the topoisomerase I inhibitor 7-ethyl-10-[4-(1-piperidino)-1-piperidino]-carbonyloxycamptothecin (CPT-11) promotes the activation of NF-κB in cells to induce resistance towards itself, and that a adenoviral transfer of an IκB, IκBα, to inhibit NFκB promotes chemosensitivity to treatment with CPT-11.

WO98/37228 teaches that an agent which decreases IKK activity or that alters the association of IKK and IκB can be useful for allowing apoptosis to occur in a tumour cell by increasing the level of unphosphorylated IκB, which can bind to NF-κB and decrease the level of active NF-κB in the tumour cell.

Rossi, Nature, 403, 103–108, 2000 teaches that cyclopentenone prostaglandins inhibit IκB kinase, and that this makes cyclopentenone prostaglandins potentially valuable in the treatment of cancers, inflammation and viral infections.

SUMMARY OF THE INVENTION

It has surprisingly been found that a certain class of cyanoguanidine derivatives is capable of modulating the activity of IκB kinase (abbreviated IKK in the following). By modulating the activity of IKK in the cells it is possible to control the level of activated NF-κB in the cells. Such cyanoguanidines are therefore considered useful in the treatment of neoplastic diseases and other conditions believed to be affected by the level of activated NFκB, e.g. inflammation.

Accordingly, in one aspect the invention relates to a method of modulating the level of activated NF-κB in cells by contacting cells with a compound of general formula I

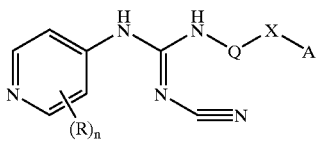

wherein
n is 0, 1 or 2;
each R independently represents halogen, trifluoromethyl, hydroxy, $C_{1-4}$ alkyl, alkoxy or alkoxycarbonyl, nitro, cyano, amino, sulfo or carboxy;
Q is straight or branched, saturated or unsaturated $C_{4-20}$ divalent hydrocarbon radical;
X is a bond, O, S, amine, carbonyl, carbonylamino, aminocarbonyl, oxycarbonyloxy, oxycarbonyl, carbonyloxy, aminocarbonyloxy, aminothiocarbonyloxy, oxycarbonylamino or oxythiocarbonylamino;
A is di-($C_{1-4}$ alkoxy)phosphinoyloxy, $C_{1-4}$ alkoxycarbonyl, $C_{1-4}$ alkoxycarbonylamino, a saturated or unsaturated $C_{3-12}$ carbocyclic ring or $C_{3-12}$ heterocarbocyclic ring optionally substituted with one or more $R_1$; $R_1$ being independently selected from the group consisting of halogen, trifluoromethyl, hydroxy, $C_{1-4}$ alkyl, $C_{1-4}$ alkoxy, $C_{1-4}$ alkoxycarbonyl, nitro, cyano, amino, carboxy, sulfo, carboxamido, sulfamoyl or $C_{1-4}$ hydroxyalkyl;
or a pharmaceutically acceptable salt, N-oxide or N-substituted prodrug thereof, in an amount effective to modulate the activity of IKK.

In another aspect, the invention relates to a method of reducing the anti-apoptotic effect of NFκB by contacting the cells with a compound of general formula I, as defined above, in an amount effective to inhibit IKK.

In a further aspect, the invention relates to a method of reducing resistance of cancer cells to chemotherapeutic agents and/or ionising radiation by contacting cancer cells with a compound of the general formula I, as defined above, in an amount effective to down-regulate the activity of IKK.

In a still further aspect, the invention relates to a method of inhibiting the IKK complex by contacting cells with a compound of general formula I, as defined above, in an amount effective to inhibit IKK.

In a still further aspect, the invention relates to a method of screening for cyanoguanidine compounds capable of inhibiting IKK or a subunit thereof, the method comprising contacting IKK or a subunit thereof or a cell expressing IKK or a subunit thereof with a cyanoguanidine compound and identifying the cyanoguanidine compound as being capable of inhibiting IKK or a subunit thereof by determining a change in NF-κB activity in the presence of said cyanoguanine compound compared to the level of NF-κB activity in the absence of said cyanoguanidine compound, or alternatively by determining a change in the phosphorylating activity of IKK in the presence of said cyanoguanine compound compared to the level of phosphorylating activity of IKK in the absence of said cyanoguanidine compound.

In a still further aspect the invention relates to the use of a compound of general formula I, as defined above, for the preparation of a medicament for the prevention or treatment of diseases or disorders associated with increased levels of NF-κB activity in cells and/or associated with upregulated IKK activity in cells and/or to reduce the resistance of cancer cells to chemotherapeutic agents and/or ionising radiation.

DETAILED DESCRIPTION OF THE INVENTION

Figure 1:
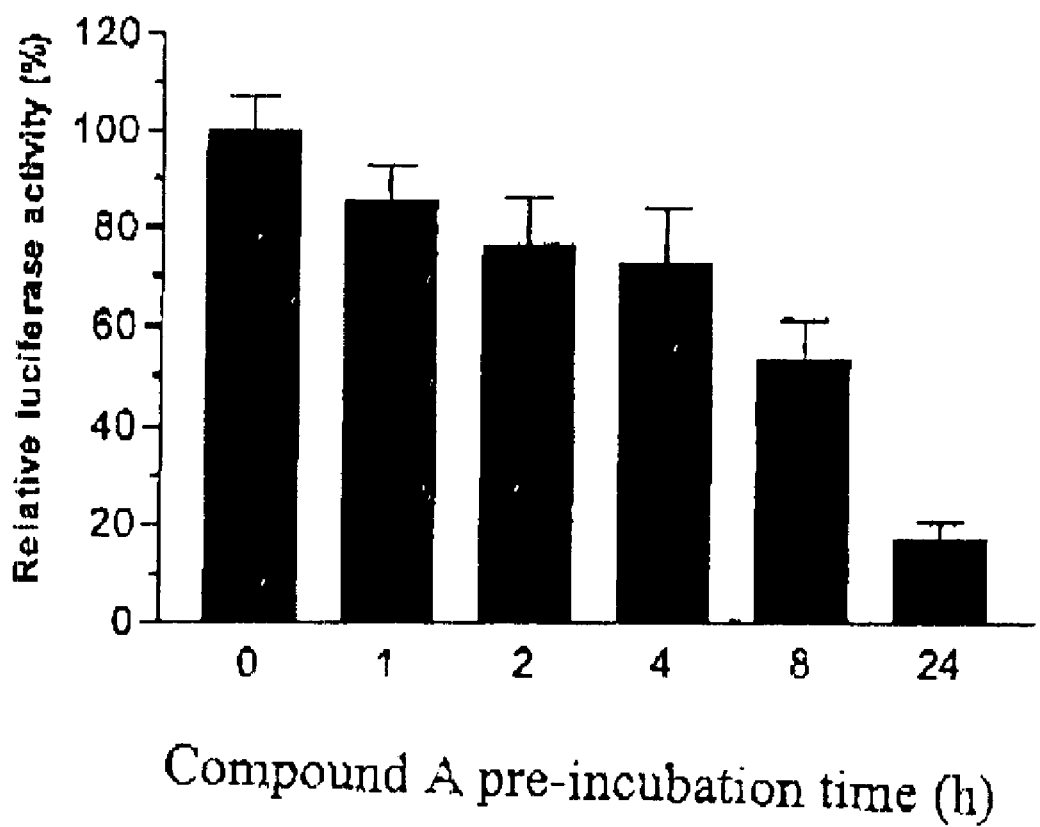
FIG. 1 shows that LPS-induced activation of the NF-κB-inducible luciferase reporter construct is suppressed after treatment with 1 μM of compound A. $3.5×10^7$ THP-1 cells were transfected with 5 μg of DNA construct. At 24 h after transfection, the cells were pre-incubated with 1 μM of compound A or 0.01% DMSO for 0, 1, 2, 4, 8, and 24 h before stimulation with 1 μg/ml LPS for additionally 5 h. Cell lysates were assayed for luciferase activity. All the results were normalised with respect to transfection efficiency. The relative luciferase activity is expressed as percent of the activity of DMSO-treated cells. The bars represent the mean (±SD) of two independent experiments performed in triplicate.

The term "alkyl" is intended to indicate a univalent radical derived from straight, branched or cyclic alkane by removing a hydrogen atom from any carbon atom. The term includes the subclasses primary, secondary and tertiary alkyl, such as methyl, ethyl, n-propyl, isopropyl, n-butyl, isobutyl, sec.-butyl, tert.-butyl, isopentyl and hexyl, cyclopropyl, cyclopentyl and cyclohexyl.

The term "divalent hydrocarbon radical" is intended to include straight or branched, saturated or unsaturated carbon chains, e.g. alkylene, alkenylene or alkynylene.

The term "alkoxy" is intended to indicate a radical of formula OR', wherein R' is alkyl as defined above, e.g. methoxy, ethoxy, propoxy, butoxy, etc.

The term "alkoxycarbonyl" is intended to indicate a radical of formula —COOR' wherein R' is alkyl as defined above, e.g. methoxycarbonyl, ethoxycabonyl, n-propoxycarbonyl, isopropoxycarbonyl, etc.

The term "carbocyclic ring" is intended to include radicals of saturated or unsaturated rings, optionally fused bicyclic rings, e.g. cyclopropyl, cyclopentyl, cyclopentenyl, cyclohexyl, cyclohexenyl, phenyl, nafthyl, dihydronafthyl, indanyl and indenyl.

The term "heterocarbocyclic ring" is intended to include radicals of saturated or unsaturated heterocyclic rings, optionally fused bicyclic rings, with one or more heteroatoms selected from O, S and N, e.g. pyridyl, tetrazolyl, thiazolyl, imidazolyl, pyrazolyl, oxazolyl, isoxazolyl, thienyl, pyrazinyl, isothiazolyl, benzimidazolyl and benzofuranyl, pyrrolyl, furanyl, pyranyl, thiophenyl, pyrazolyl, pyrrolidinyl, pyridinyl, pyrimidinyl, tetrahydrotiophenyl, tetrahydrofuranyl, tetrahydropyranyl, piperidinyl, putinyl, quinolinyl, isoquinolinyl, 1,2-dihydroquinolinyl, etc.

The term "halogen" is intended to indicate fluoro, chloro, bromo or iodo.

The term "pharmaceutically acceptable salt" is intended to indicate salts prepared by reacting a compound of formula I comprising a basic group with a suitable inorganic or organic acid, e.g. hydrochloric, hydrobromic, hydroiodic, sulfuric, nitric, acetic, phosphoric, lactic, maleic, phthalic, citric, propionic, benzoic, glutaric, gluconic, methanesulfonic, salicylic, succinic, tartaric, toluenesulfonic, sulfamic or fumaric acid. Pharmaceutically acceptable salts of compounds of formula I may also be prepared by reaction with a suitable base such as sodium hydroxide, potassium hydroxide, ammonia or the like.

The term "N-oxide" is intended to indicate e.g. pyridyl N-oxide derivatives of the compounds of the invention. Such compounds may be prepared by oxidation of the pyridyl N by a suitable oxidising agent, e.g. 3-chloroperbenzoic acid in an inert solvent, e.g. dichlormethan. Other suitable methods to improve the physico-chemical properties and/or solubility of the compounds of the present invention, e.g. prodrugs, are known in the art, and they are also included in the present invention.

The term "N-substituted prodrug" is intended to indicate a cyanoguanidine compound of formula I comprising a substituent at the N atom of the pyridyl ring. The substituent is intended, i.e., to improve the solubility of compounds of formula I and is designed to be cleaved off in viva upon administration of the prodrug. Examples of such prodrugs are disclosed in co-pending International Patent Application No. PCT/DK01/00750 which is hereby incorporated by reference herein in its entirety.

The term "resistance" is intended to indicate a reduced sensitivity to a given treatment. Sensitivity can be defined in terms of $IC_{50}$, which indicates the amount or concentration of a given treatment or ionising radiation which is lethal to 50% of the cells. An increase in $IC_{50}$ signifies a reduced sensitivity to a given therapy, and the cells are termed "resistant" if $IC_{50}$ increases by a factor of 10 or more, e.g by a factor of 20–50. This definition is of particular relevance for in vitro studies, but of less relevance for in vivo studies, not to mention treatment of human beings. For in vivo studies and in human therapy a more feasible definition of resistance may be expressed as the overall failure of treatment, defined as progressing neoplastic diseases in a patient who previously responded to treatment. Progressing neoplastic diseases may be defined as ≧25% increase in the size of one or more lesions or the appearance of new lesions [*WHO Handbook for reporting results of cancer treatment*, Publication No. 48, Geneva, WHO, 1979]. A compound capable of revitalising a treatment to which cells or patients are resistant is said to reduce resistance to said treatment. A compound said to reduce resistance may lower the level of $IC_{50}$ by a factor of 10 or more, e.g. by a factor of 20–50. Similarly, a compound said to reduce resistance to a treatment will generally restore treatment response, Resistance to treatment of neoplastic diseases is caused by the ability of individual cells to avoid the lethal effect of the treatment. Cells capable of avoiding the lethal effect of the treatment have a proliferative advantage compared to cells sensitive to the treatment. In the course of a treatment the number of resistant cells will thus increase at the expense of the number of sensitive cells. The cells in e.g. a cancer tumour and in the same cancer tumour in a resistant state, accordingly, have different characteristics and are thus not identical.

The term "modulate" when used in relation to levels of activated NF-κB means that the level of transcriptionally active NF-κB (rather than NF-κB that is merely translocated from the cytosol to the nucleus) is increased or decreased compared to the level present in the absence of a compound of general formula I. The level of activated NF-κB is preferably reduced by the compound of formula I.

The term "down-regulation" is intended to indicate a decrease in the expression level of a gene or a decrease in the level of activity of a gene product. Conversely, the term "upregulation" is intended to indicate an increase in the expression level of a gene or an increase in the level of activity of a gene product.

The term "cyanoguanidine compound" is intended to indicate a compound comprising the structure shown in formula II

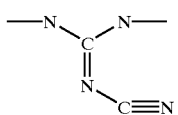

The term comprises, but is not limited to compounds of general formula I, e.g. cyanoguanidine compounds disclosed in WO 00/61559, WO 00/61561, WO 00/76516 and WO 00/76517 are also included in this definition.

Preferred compounds of formula I are those wherein A is a phenyl, optionally substituted with a substituent selected from the group consisting of halogen, trifluoromethyl, hydroxy, $C_{1-4}$ alkyl, $C_{1-4}$ alkoxycarbonyl, nitro, cyano, amino, carboxy, sulfo, carboxamido, sulfamoyl or $C_{1-4}$ hydroxyalkyl.

In a further preferred embodiment of the invention X is O.

In a still further preferred embodiment of the invention X is a bond and A is di-($C_{1-4}$ alkoxy)phosphinoyloxy.

In a still further preferred embodiment of the invention Q is a $C_{4-12}$ divalent hydrocarbon radical.

In a still further preferred embodiment of the invention n is 0 or n is 1, R being $C_{1-4}$ alkoxy.

In a still further preferred embodiment of the invention the compound of formula I is selected from the group consisting of N-(6-(4-chlorophenoxy)hexyl)-N'-cyano-N"-(4-pyridyl) guanidine, N-cyano-N'-(9-diethylphosphionyloxynonyl)-N"-(4-pyridyl)guanidine, N-(6-(4-chlorophenoxy)hexyl-N"-cyano-N"-(2-methoxy-5-pyridyl) guanidine, or N-(tert-butoxycarbonylamino-dodecyl)-N'-cyano-N"-(4-pyridyl)guanidine.

Compounds of general formula I contain asymmetric carbon atoms, ring systems as well as carbon—carbon double bonds, which allows for isomeric forms. It is understood that the present invention relates to any tautomeric, diastereomeric and optical isomeric form expressed by general formula I either in pure form or as mixtures thereof.

NF-κB is a member of the Rel family of transcription factors which are ubiquitous in animal cells. Rel proteins can form dimers, the most common of which is designated NF-κB, NF-κS is a p50/p65 heterodimer which can activate transcription of genes containing the appropriate κB binding site. In non-stimulated cells, NF-κB is maintained in the cytoplasm by interaction with NF-κB inhibiting proteins, the IκBs. In response to cell stimulation by e.g. anti-neoplastic drugs or ionising radiation an IκB kinase complex (IKK) is rapidly activated and phosporylates two serine residues in the NF-κB binding domain of IκB. The phophorylated IκB is then degraded by a 26S proteasome whereas NF-κB is spared from degradation and translocates into the nucleus [Wang, Science, 274, 784–787, 1996, Cusak, Cancer Research, 60, 2323–2330, 2000; Karin, Immunology, 12, 2000, 85–98]. NF-κB is thus always present in the cell, but in an inactivated form in non-stimulated cells. After translocation into the nucleus NF-κB induces inter alia the anti-apoptotic genes c-IAP1, c-IAP2, TRAF1, TRAF2, Bfl-1/A1, Bcl-$X_L$ and Mn-SOD [Patel, Oncogene, 19, 2000, 4159–41699], which bring about resistance in the cells to apoptosis. This effect is referred to as the anti-apoptotic effect of NF-κB, and the effect may be quantified by measuring the expression of gene products encoded by any of said genes, by any suitable means known in the art, in the presence and absence of compounds modulating the level of activated NK-κB. Any compound capable of reducing the transcription of one or more of said genes to a level of less than about 50%, e.g. less than about 30%, such as less than about 20% of the level in the absence of said compound is said to reduce the anti-apoptotic effect of NK-κB. Antineoplastic drugs and ionising radiation thus induce resistance in the cells to the treatments, which render them ineffective. Accordingly, activated NF-κB is a key factor in induced resistance in e.g. cancer cells to chemotherapeutic drugs and/or to ionising radiation. This is further supported by the fact that constitutively activated NF-κB is found in cells from resistant cancer tumours [Patel, Oncogene, 19, 4159–4169, 2000]. Regardless of reduced resistance to any treatment, a reduction of the level of activated NF-κB in the cell, e.g. by controlling the activity of IKK, will reduce the expression levels of genes encoding for anti-apoptotic factors, thereby inducing apoptosis in the cells [Schwartz, Surgical Oncology, 8, 1999, 143–153].

The role of activated NF-κB is not restricted to preventing apoptosis. NF-κB is also a critical activator of genes involved in inflammation and immunity. Activated NF-κB induces the gene coding for cyclooxygenase 2 (COX2), which catalyses the synthesis of pro-inflammatory prostaglandins. Furthermore, at later stages in an inflammatory episode, COX2 catalyses the synthesis of the anti-inflammatory cyclopentenone prostaglandins. COX2 is also known to have anti-viral effects, which suggests that NF-κB may also be a target in the therapy of inflammatory and viral diseases [Rossi, Nature, 403, 2000, 103–108]. NF-κB is also responsible for the transcriptional regulation of genes important for many other vital cellular processes. NF-κB e.g. regulates genes encoding cytokines and growth factors, adhesion molecules, acute phase reactants, receptors and chemoattractants [Schwartz, Surgical Oncology, 8, 1999, 143.153].

IκB is non-covalently bound to NF-κB and masks its nuclear localisation signal, thereby preventing translocation into the nucleus. Various IκBs have been identified and e.g. IκBα and IκBβ are expressed in most cells where they bind to p65 Rel proteins, i.e. NF-κB. Different IκB are phosphorylated by different factors allowing activation of NF-κB in response to different stimuli.

The IκB kinase complex (IKK) consist of three subunits, namely IKKα, IKKβ and IKKγ, with a combined molecular weight of 900 kDa. IKKα and IKKβ both exhibit IκB kinase activity and phophorylate IκB, whereas IKKγ is a regulatory subunit. IKKα is 85 kDa protein and IKKβ is a 87 kDa protein, and the two subunits show a large degree of homology. Whereas both IKKα and IKKβ are catalytically active, it has surprisingly been shown that only IKKβ is essential for IKK phosphorylation of IκB. It has been found by the present inventors that compounds of general formula I are effective as inhibitors of IKKβ in particular.

Furthermore, kinase profiling against about 40 different kinases has established that compounds of formula I are surprisingly selective for IKK and show little or no reactivity against the other kinases tested. This suggests a specific and unexpected effect of compounds of formula I rather than a general toxic effect.

As described above, controlling the level of activated NF-κB by controlling the activity of IKK may be useful as therapeutic intervention in the treatment of neoplastic diseases, e.g. cancers and in particular resistant cancer forms. Controlling the activity of IKK may also be useful in the treatment of inflammatory or viral diseases. Controlling the activity of IKK may either be as a single agent therapy, or it may be part of a combination treatment with other treatments, such as one or more of the conventional antineoplastic treatments discussed above.

Compounds of formula I are known from the literature and methods of their synthesis have previously been disclosed [EP660 823, WO 98/54141, WO 98/54143 and WO 98/54145]. While the compounds have previously been suggested for cancer therapy, there is no indication in the literature that these compounds may be used specifically to target IKK activity and thus prevent NF-κB from exerting its anti-apoptotic effect. Likewise, it has not been suggested that compounds of formula I might be of particular use in the treatment of cancers resistant to other forms of treatment.

The methods of the present invention may be carried out in vivo or in vitro. For in vitro purposes, the present method may e.g. be used for screening of cyanoguanidine compounds in order to identify new cyanoguanidine compounds capable of modulating the activity of IKK or subunits thereof. Such a screening assay may comprise e.g. isolated IKK or subunits thereof exposed to cyanoguanidine compounds suspected to modulate IKK activity. Methods of obtaining isolated IKK or subunits thereof are known in the art. They comprise e.g. immunoprecipitation or expression of IKK or subunits thereof in a suitably selected host cell, e.g. as disclosed in WO98/37228. The IKK activity may conveniently be measured by determining phosphorylation of e.g. IκB, either directly or by using antibodies against phophorylated IκB. Other suitable substrates for IKK may also be used. The screening assay may also be a cellular assay in which cells expressing IKK or subunits thereof are exposed to cyanoguanidines suspected of modulating IKK activity. The cells in a cellular assay may be manipulated to enhance the expression level of IKK or subunits thereof. Methods for manipulating the expression level of proteins in cells are known in the art examples of which are genetic manipulation, classic mutation and selection. Following exposure for an appropriate amount of time, the cells may be collected, lysed, and the IKK Immunoprecipitated using an appropriate antibody. A substrate, IκB or another suitable substrate may then be added to the immunocomplex, and its ability to phosphorylate the substrate may be determined as described above, and the result compared to the result from a similar experiment performed in the absence of a cyanoguanidine compound.

The ability of cyanoguanidine compounds to modulate the activity of IKK or subunits thereof in a cellular assay may also be determined without disrupting the cells through lysis. After exposure of the cells to a cyanoguanidine compound for an appropriate amount of time, the secretion from the cells of e.g. specific cytokines regulated by NF-κB may be measured. Examples of such specific cytokines are tumour necrosis factor a (TNFα) and interleukin 10 (IL-10). The result is compared to results from similar experiments conducted in the absence of cyanoguanidine compounds. The specific compounds regulated by NF-κB and secreted by the cell may vary between different types of cells. A person skilled in the art is capable of choosing which compound or compounds will be most relevant measure for a given cell system.

Regardless of how an IKK assay is run, a compound which reduces the activity of either IKK or the level of activated NF-κB to a level less than about 50%, e.g. less than about 30% or even less than about 20% of the level in the absence of said compound is said to inhibit IKK or to reduce the level of activated NKκB, respectively.

The present method may also be carried out in vivo, e.g. by administering an effective amount of a cyanoguanidine compound, either alone or as part of a combination treatment, to a patient in need thereof in order to modulate the level of activated NF-κB in such a patient's cells. To that end, it is preferred to administrate the compound of formula I as an active ingredient in a pharmaceutical formulation. Conveniently, the active ingredient comprises from 0.1 ppm to 100% by weight of the formulation.

In the formulation, the active ingredient is present in association with a pharmaceutically acceptable vehicle and optionally one or more other therapeutic ingredients. The vehicle must be "pharmaceutically acceptable" in the sense of being compatible with the other ingredients of the formulations and not deleterious to the recipient thereof. The formulation may be in a form suitable for oral, ophthalmic, rectal, parenteral (including subcutaneous, intramuscular, interperitoneal, intraarticular and intravenous), transdermal, and topical, nasal or buccal administration.

The formulations may conveniently be presented in dosage unit form and may be prepared by any of the methods well known in the art of pharmacy, e.g. as disclosed in Remington, *The Science and Practise of Pharmacy*, 20$^{th}$ Ed., 2000. All methods include the step of bringing the active ingredient into association with the vehicle which constitutes one or more auxiliary constituents. In general, the formulations are prepared by uniformly and intimately bringing the active ingredient into association with a liquid vehicle or a finely divided solid vehicle or both, and then, if necessary, shaping the product into the desired formulation.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Formulations suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose and polyvinylpyrrolidone. The active ingredient may also be administered in the form of a bolus, electuary or paste.

A tablet may be prepared by compressing or moulding the active ingredient optionally with one or more auxiliary constituents. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose polyethylene glycol, waxes or the like; a lubricant such as e.g. sodium oleate, sodium stearate, magnesium steatrate, sodium benzoate, sodium acetate, sodium chloride or the like; a disintegrating agent such as e.g. starch, methyl cellulose, agar, bentonite, xanthan gum or the like or dispersing agent. Moulded tablets may be made by moulding, in a suitable machine, a mixture of the powdered active ingredient and suitable carrier moistened with an inert liquid diluent.

Formulations for rectal administration, e.g. injection or infusion, may be in the form of a suppository incorporating the active ingredient and a vehicle, or in the form of an enema.

Formulations suitable for parenteral administration may conveniently comprise a sterile oily or aqueous preparation of the active ingredients, which is preferably isotonic with the blood of the recipient, e.g. an isotonic saline, isotonic glucose solution or buffer solution. Liposomal formulations may also be used to present the active ingredient for parenteral administration. The formulation may conveniently be sterilised by for instance filtration through a bacteria retaining filter, addition of sterilising agent to the formulation, irradiation of the formulation or heating of the formulation.

Alternatively, the formulation may be provided as a sterile, solid preparation, e.g. a freeze-dried powder, which is readily dissolved in a sterile media just prior to use.

Transdermal formulations may be in the form of a plaster.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems may also be used to present the active ingredient for ophthalmic administration.

Formulations suitable for topical or ophthalmic administration include liquid or semi-liquid preparations such as liniments, lotions, gels, oil-in-water or water-in-oil emulsions such as creams, ointments or pastes; or solutions or suspensions such as drops.

In addition to the aforementioned ingredients, the formulations comprising a compound of formula I may include one or more additional ingredients such as diluents, buffers, flavouring agents, colourants, surface active agents, thickeners, preservatives, e.g. methyl hydroxybenzoate (including anti-oxidants), emulsifying agents and the like.

In addition to the formulations described above, compounds of formula I may also be formulated as a depot preparation. Such long-acting formulations may be administered by implantation (e.g. subcutaneously or intramuscularly) or by intramuscular injection. Thus, for example, the active ingredient may be formulated with suitable polymeric or hydrophobic materials (for example as an emulsion in a pharmaceutically acceptable oil), or an ion exchange resin.

For systemic treatment according to the present invention, daily doses of from 0.001–100 mg/kg body weight, preferably from 0.002–15 mg/kg of mammal body weight, for example 0.003–10 mg/kg of a compound of formula I are administered, typically corresponding to a daily dose for an adult human of from 0.2 to 750 mg of the active ingredient. In the topical treatment of dermatological disorders, ointments, creams or lotions containing from 0.1–750 mg/g, and preferably from 0.1–500 mg/g, of a compound of formula I may be administered. For topical use in ophthalmological ointments, drops or gels containing from 0.1–750 mg/g, and preferably from 0.1–500 mg/g, of a compound of formula I are administered. Oral compositions are formulated, preferably as tablets, capsules, or drops, containing from 0.05–250 mg, preferably from 0.1–125 mg, of a compound of formula I per dosage unit.

As discussed above, the invention relates to methods of modulating levels of activated NF-κB, reducing the anti-apoptotic effect of NF-κB or inhibiting IKK in neoplastic and cancer cells. These cells may be hematological cancer cells, such as leukaemia cells, acute myeloid leukaemia cells, chronic myeloid leukaemia cells, myelodysplasia cells, multiple myeloma cells, Hodgkin's disease cells or non-Hodgkin's lymphoma cells or solid tumour cells such as, lung carcinoma cells (small or non-small cell), gastric, intestinal or colorectal cancer cells, prostate, ovarian or breast cancer cells, brain cancer cells, head and neck cancer cells, cells from cancer in the urinary tract, such as kidney or bladder cancer cells, malignant melanoma cells, lever cancer cells, uterine or pancreatic cancer cells, etc.

In a preferred embodiment, these cancer cells have become resistant to medicaments for treatment of neoplastic diseases such as chemotherapeutic agents, hormonal agents and biological response modifiers, indicated above and/or to ionising radiation.

The invention is further illustrated in the following examples which are not in any way intended to limit the scope of the invention as claimed.

EXAMPLES

Materials

Compounds

In vitro experiments. The following compounds were used in the experiments;

N-(6-(4-chlorophenoxy)hexyl)-N'-cyano-N"-(4-pyridyl) guanidine (compound A)

N-(tert-butoxycarbonylamino-dodecyl)-N'-cyano-N"-(4-pyridyl)guanidine (compound B)

N-(6-(4-chlorophenoxy)hexyl-N"-cyano-N"-(2-methoxy-5-pyridyl) guanidine (compound C)

N-(3-nitrophenoxy)hexyl-N'-cyano-N"-phenylguanidine (compound D)

N-(4-chlorophenoxy)hexyl-N'-cyano-N'-(3-ethoxycarbonylphenyl)guanidine (compound E)

(Department of Chemical Research, Leo Pharmaceutical Products). The compounds were dissolved at 10 mM in DMSO and stored at −20° C.

In vivo experiments. For dilution of compounds A, B, C, D and E, a mixture of 2% carboxymethyl cellulose and demineralised water was used.

Cells. The THP-1 (TIB-202), Colo-320 (CCL-220), HT-1080 (CCL-121) and PC-3 (CRL-1435) cell lines were all obtained from American Type Culture Collection (Rockville, Md.). The NYH SCLC cell line was a gift from P. Buhl Jensen (Rigshospitalet, Copenhagen, Denmark). All cell culture products were purchased from Gibco BRL (Gaithersburg, Md.).

The human monocytic derived THP-1 cell line was maintained at a cell density between $1 \times 10^5$ to $1 \times 10^6$ cells/ml in a culture medium consisting of RPMI 1640 supplemented with 2 mM L-glutamine, 100 μg/ml streptomycin, 100 IU/ml penicillin, and 10% low endotoxin foetal bovine serum (FBS; less than 1 endotoxin U/ml).

Colo-320 is a human colon adenocarcinoma cell line. The cells are semi-adherent and grown in RPMI 1640 supplemented with 10% FBS, 2 mM L-glutamine, 1 mM pyruvate, 2 g/l glucose, 100 IU/ml penicillin and 100 μg/ml streptomycin.

HT-1080 is a human fibrosarcoma cell line. The cells are semi-adherent and were cultured in DMEM supplemented with 10% FBS, 2 mM L-glutamine, 1% non essential amino acid, 100 IU/ml penicillin and 100 μg/ml streptomycin.

The PC-3 is a human prostate adenocarcinoma cell line. The cells are adherent and cultured in HAM's F-12K supplemented with 10% FBS, 2 mM L-glutamine, 100 IU/ml penicillin and 100 μg/ml streptomycin.

The NYH SCLC is a small cell lung cancer cell line. The cells are semi-adherent and cultured in RPMI 1640 with the addition of 10% FBS, 2 mM L-glutamine, 100 IU/ml penicillin and 100 μg/ml streptomycin.

Example 1

Inhibition of NF-κB Dependent Gene Transcription and NF-κB DNA Binding Activity

Methods

Luciferase plasmids: The NF-κB-luciferase reporter plasmid (pBIIX) was a gift from Marja Jäättelä and Ida S. Mathiasen, the Danish Cancer Society. It was constructed by inserting a synthetic fragment with two copies of the sequence (5'-ACA GAG GGG ACT TTC CGA GAG-3' separated by four nucleotides (5'-ATCT-3') in front of a mouse fos promoter in a plasmid pfLUC (a pBluescript-based plasmid with a firefly luciferase encoding sequence) (K. Saksela and D. Baltimore, Mol. Cell Biol. 13, 1993, pp. 3698–3705) The NF-κB binding site from the mouse Igκ light chain is underlined (M. Grilli et al., Int. Rev, Cytol. 143, 1993, pp. 1–62). A Renilla luciferase plasmid with a thymidine kinase promoter (pRL-TK vector) was used as a control for transfection efficiency and was obtained from Promega Inc., Madison, Wis. Plasmid DNA was prepared and purified using the QIAGEN EndoToxin-free Maxiprep-500 kit (QIAGEN, Hilden, Germany).

Transfection assays: THP-1 cells were transiently transfected during the log phase of growth using a DEAE-dextran transfection procedure (modified from J. Yao et al., J. Biol. Chem. 272, 1997, pp. 17795–17801). Approximately 3.5× $10^7$ cells were resuspended in 1 ml transfection medium (RPMI 1640 supplemented with 2 mM L-glutamine) and incubated with 5 μg of construct DNA, 0.5 μg pRL-TK vector plus 500 μg of DEAE-dextran (Sigma-Aldrich). Addition of 10 ml of the transfection medium stopped the transfection. After having been washed with the transfection medium, the cells were resuspended in 7 ml of culture medium. The cells were then distributed into 24-well plates (NUNC, Roskilde, Denmark), each well containing 250 μl of cell suspension (approximately 1.25×$10^6$ cells) and 1.25 ml culture medium, and they were incubated for 24 h before treatment. Compound A or DMSO was added to the wells 24 h prior to stimulation with 1 μg/ml LPS for 5 h. All fluids and dilutions were made with endotoxin free water.

The THP-1 cells were harvested, pelleted by centrifugation and washed with 1×PBS before being resuspended in 50 μl of lysis buffer.

The cell lysate was assayed for luciferase activity using the Dual luciferase kit as described by the manufacturer (Promega). All transfections were performed in triplicate. Firefly luciferase activity was corrected for differences in transfection efficiency by normalizing it to the measured Renilla luciferase activity.

EMSA: For preparation of nuclear extracts, $10^7$ cells were used at each experimental point. Following treatment of the THP-1 cells with either 1 μM of compound A for 24 h and stimulation with 1 μg/ml LPS at the indicated times, the cells were washed twice in PBS, and the cells were extracted for protein. The cells were resuspended in 500 μl buffer A (20 mM HEPES (pH 7.8), 0.1 mM EDTA, 10 mM KCL) with a protease inhibitor mixture (1 mM DTT, 0.5 mM Pefablock). Afterwards, the cells were incubated on ice for 15 min, then 30 μl 10% NP 40 was added and the cells were centrifuged at 5000×g. Each cell pellet was then resuspended in 50 μl buffer B (buffer A with 400 mM NaCl) and vortexed, followed by incubation for 15 min at 4° C. and centrifugation at 5000×g for 5 min at 4° C. The supernatant from each cell pellet was collected and the protein concentration quantified using the BCA-200 protein assay kit from Pierce (Rockford, Ill., USA). The nuclear extracts were stored at −80° C.

Double-stranded κB oligos (5'-AGT TGA GGG GAC TTT CCC AGG C-3' and the complement strand) were purchased from Promega. The κB oligonucleotides were endlabelled with [γ-$^{32}$P]ATP (Amersham Pharmacia Biotech) using T4 polynucleotide kinase (Gibco BRL). Unincorporated label was separated using a Sephadex G50 spin column (Amersham Pharmacia Biotech). For the binding reaction, 200,000 cpm of radiolabelled κB oligonucleotide probe was incubated with 10 μg of nuclear extract in binding buffer (1 mM Tris-HCl (pH 7.5), 50 mM NaCl, 3 mM $MgCl_2$, 0.5 mM DTT, 0.05% NP-40) in the presence of 3 μg poly(dI-dC) (Amersham Pharmacia Biotech) as a stabilizer of the protein/DNA complex. Unlabelled κB oligonucleotides were added to one lane as a specific competitor and an antibody against the NF-κB subunit p65 (Santa Cruz Biotechnology Inc.) was added to the other lane for the super shift experiment. The reaction mixture was incubated for 30 min. at room temperature and loaded on a 5% nondenaturing polyacrylamide gel in 1×TAE buffer. After electrophoresis at 4° C., the gel was dried, and the protein-DNA complexes were visualized and quantified on the STORM 860 Phospholmager using the ImageQuaNT software (available from Molecular Dynamics).

Results

Luciferase activity: LPS is one of the most potent activator of the NF-κB signaling pathway. To investigate whether compound A could modulate this effects of LPS on the activity of NF-κB, we performed a series of experiments where THP-1 cells, co-transfected with the NF-κB-dependent luciferase reporter construct and a control plasmid, were cultured for 0, 1, 2, 4, 8, and 24 h in the presence of 1 μM of compound A. LPS was then added and the incubation continued for another 5 h. The cells were lysed and the luciferase activity was determined. All samples were made in triplicate and they were normalized with respect to transfection efficiency and expressed as percent of the activity of the DMSO-treated cells (FIG. 1). After a pre-incubation time of 2 h, a small decrease in the NF-κB-dependent luciferase activity was observed and this decrease continued, so after a preincubation time of 24 h the NF-κB-dependent induction of luciferase expression was blocked by almost 80%.

Figure 2A:
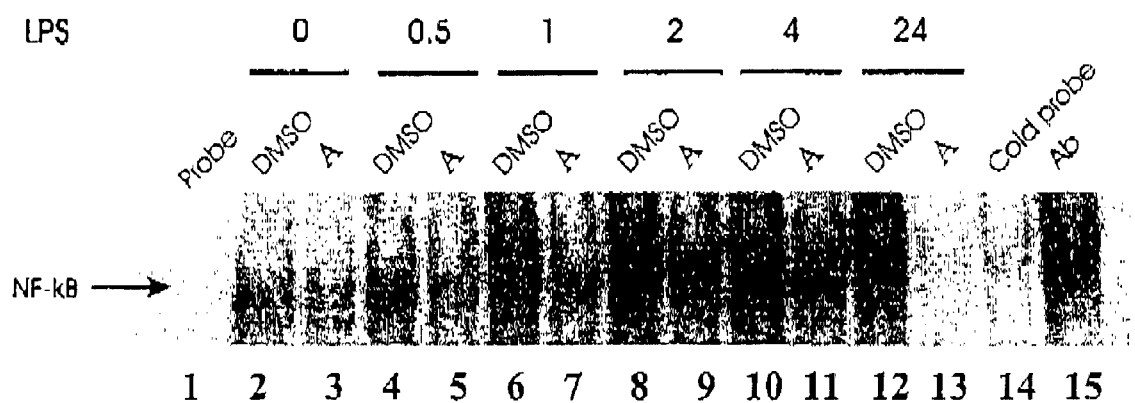
FIG. 2 shows that treatment of THP-1 cells with compound A before stimulation with LPS Inhibits the nuclear localisation of NF-κB. The THP-1 cells were pre-incubated with 1 μM of compound A or 0.01% DMSO for 24 h followed by an additional stimulation with 1 μg/ml LPS for the indicated times. The amount of NF-κB in the nuclear extracts was analysed by allowing it to bind to a radiolabelled NF-κB consensus oligonucleotide. Protein-DNA complexes were resolved by nondenaturing PAGE on a 5% gel and visualised (A) and quantified (B) on a Phospholmager. The migration position of NF-κB complexed with labelled DNA, which was competed by excess unlabelled probe (lane 14) and super shifted with an antibody against the p65 subunit (lane 15), is indicated. The quantitative data is presented as percent of the DMSO control and reflect the mean (±SD) of two independent experiments.
Figure 2B:
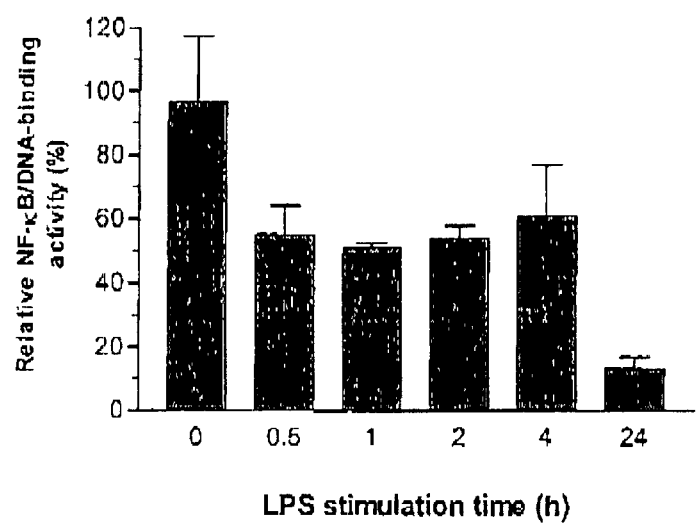

NF-κB DNA binding activity: NF-κB has to be released from its inhibitory protein, IκB in the cytosol in order to migrate to the nucleus and activate target gene expression. To delineate the role of compound A on NF-κB translocation from the cytosol to the nucleus, EMSA was carried out using nuclear extracts from LPS-stimulated THP-1 cells. In unstimulated THP-1 cells treated with either DMSO (0.01%) or compound A (1 μM), the binding of the NF-κB complex was low (FIG. 2A, lane 2 and 3), whereas stimulation with LPS (1 μg/ml) for 0.5 h and up to 4 h resulted in a distinct increase in the NF-κB binding activity in the DMSO-treated cells (FIG. 2A, lane 4, 6, 8 and 10, respectively). This increase was not observed in the compound A-treated cells (FIG. 2A, lane 5, 7, 9 and 11, respectively). After 24 h of LPS stimulation the NF-κB binding activity was slightly reduced in the DMSO-treated cells (FIG. 2A, lane 12). A super shift experiment (FIG. 2A, lane 15), performed with an antibody specific for the p65 subunit of the NF-κB, identified the position of the protein-DNA complex, as did the competition experiment (FIG. 2A, lane 14). The intensity of the protein-DNA complex was quantified using a PhosphoImager (available from Molecular Dynamics) and the results are presented in FIG. 2B, The NF-κB DNA-binding activity of THP-1 cells treated with compound A is suppressed 2-fold compared to the control after 0.5 to 4 h of LPS-stimulation and 5-fold after 24 h of LPS-stimulation.

Example 2

Prevention of LPS Induced Degradation of IκB

Methods

Western blotting: THP-1 cells ($5 \times 10^6$ cells) were starved overnight at 37° C., 5% $CO_2$ in starvation medium (RPMI 1640 with 2% FBS) including 1 μM of compound A or 0.01% DMSO. The cells were hereafter stimulated with 1 μg/ml LPS (*E. coli* serotype 055: B5, Sigma-Aldrich Danmark AS, Vallensbaek Strand, Denmark) at the indicated times. Whole cell extracts were prepared in lysis buffer (50 mM HEPES, pH 7.5, 150 mM NaCl, 10 mM EDTA, 10 mM $Na_4P_2O_7$, 100 mM NaF, 2 mM $Na_3VO_4$, 1% Triton-X-100, 0.5 mM Pefabloc (Boehringer Mannheim GmbH, Mannheim, Germany), 10 μg/μl leupeptin, 10 μg/μl aprotinin).

A 3×SDS-sample buffer (125 mM Tris/HCl pH 6.8, 4% SDS, 20% glycerol, 0.025% bromphenol blue, 10% DTT) was added to 200 μl of clarified cell lysate, and the sample (20 μl) was boiled and electrophoresed on a 12% SDS-polyacrylamide gel. The primary antibodies (anti-IκBα, anti-IκBβ, anti-cdk-7; all from Santa Cruz Biotechnology Inc., Heidelberg, Germany) were diluted 1:1000. The secondary antibody (anti-rabbit-HRP from DAKO A/S, Glostrup, Denmark) was used in a 1:2000 dilution. The signals on the nitrocellulose membrane were developed by ECL (Amersham Pharmacia Biotech, Hørsholm, Denmark). Afterwards, the same nitrocellulose membrane was stripped (100 mM β-mercaptoethanol, 2% SDS, 62.5 mM Tris pH 6.8) for 30 min. at 50° C., and the nitrocellulose membrane was reprobed with anti-Cdk7 antibodies for verification of the protein loading. The relative amounts of the transferred proteins were quantified by using the ImageQuant Software (Molecular Dynamics, Sunnyvale, Calif., USA) by scanning the autoradiographic films and normalized to the related cdk-7 amounts.

Results

Figure 3:
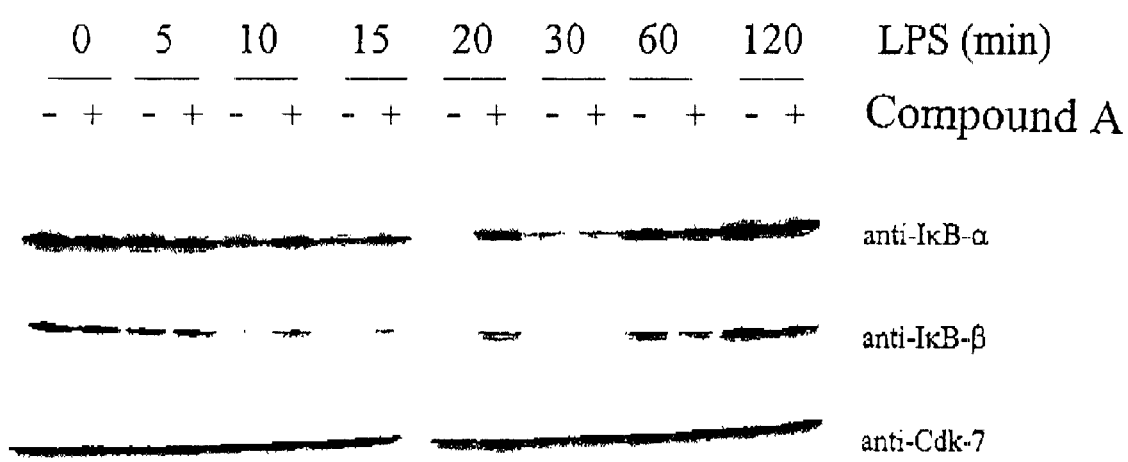
FIG. 3 shows that treatment of THP-1 cells with compound A before stimulation blocks the LPS-induced degradation of IκBα in THP-1 cells. THP-1 cells ($5×10^6$) were suspended in medium with 2% FCS and 1 μM of compound A or 0.01% DMSO for 24 h before stimulation with 1 μg/ml LPS for 0, 5, 10, 15, 20, 30, 60, and 120 min. Cell lysates were subjected to SDS-PAGE and the separated proteins were transferred to a nitrocellulose membrane. The same membranes were incubated with specific antibodies raised against the different IκB isoforms as well as with anti-cdk-7, A representative blot from two independent experiments is presented.

IκB degradation: To examine the effect of compound A on IκB stability, the THP-1 cells were treated with 1 μM of compound A or 0.01% DMSO for 24 h before LPS stimulation (FIG. 3). In unstimulated THP-1 cells treated with either DMSO or compound A, no differences in the amount of IκBα or IκBβ were observed. Stimulation with LPS for 10 to 30 min. rapidly resulted in a distinct decrease of the IκBα form in the DMSO-treated THP-1 cells and to a much lesser degree the IκBβ form. This decrease was not observed in the compound A-treated cells, where the IκB degradation occurred at a much slower rate. However, no IκBα or IκBβ proteins were detected after 30 min. in either compound A- or DMSO-treated cells. The resynthesis of the IκB's was slightly faster in the DMSO-treated cells but after 120 min of LPS-stimulation, no differences were observed between the DMSO- and the compound A-treated THP-1 cells.

Example 3

Inhibition of LPS-Induced IKK Activity

Methods

In vitro kinase assay: THP-1 cells ($1 \times 10^7$ cells) were stimulated with 1 μg/ml LPS for the indicated time periods and whole cell extracts were prepared as described above. IKK was immunoprecipitated with an IKKα/β antibody (raised against amino acid 470–755 of IKKβ of human origin but partially cross-reactive with IKKα as detected by Western Blotting (Santa Cruz Biotechnology Inc.). Compound A was diluted in kinase buffer (25 mM HEPES pH 7.5, 10 mM magnesium acetate, 50 μM ATP) at the appropriate concentrations. The compound was added to the beads for 30 min. at 30° C. The kinase reaction was started by adding 2.5 μg of the GST-IκBα substrate (Santa Cruz Biotechnology Inc.) together with 2 μCi γ-$^{32}$P-ATP (Amersham Pharmacia Biotech) per sample. The reaction was allowed to proceed for 30 min. at 30° C., and the IKK activity was measured by the amount of radioactive-labelled GST-IκBα bands, quantified by the STORM860 Phospho-Imager.

A general problem with the kinase assay is prestimulation of the kinase. To achieve a value for the zero-point, the LPS-activated IKK mixture was incubated with 20 μM myricetin (Sigma-Aldrich), which is a known IKKβ inhibitor (S. H. Tsai et al., *J. Cell Biochem.* 74, 1999, pp. 606–615). This value was subtracted from the all other values. All data are expressed as percentage of the activity of the LPS-activated IKKβ kinase treated with 0.1% DMSO.

Results

Figure 4:
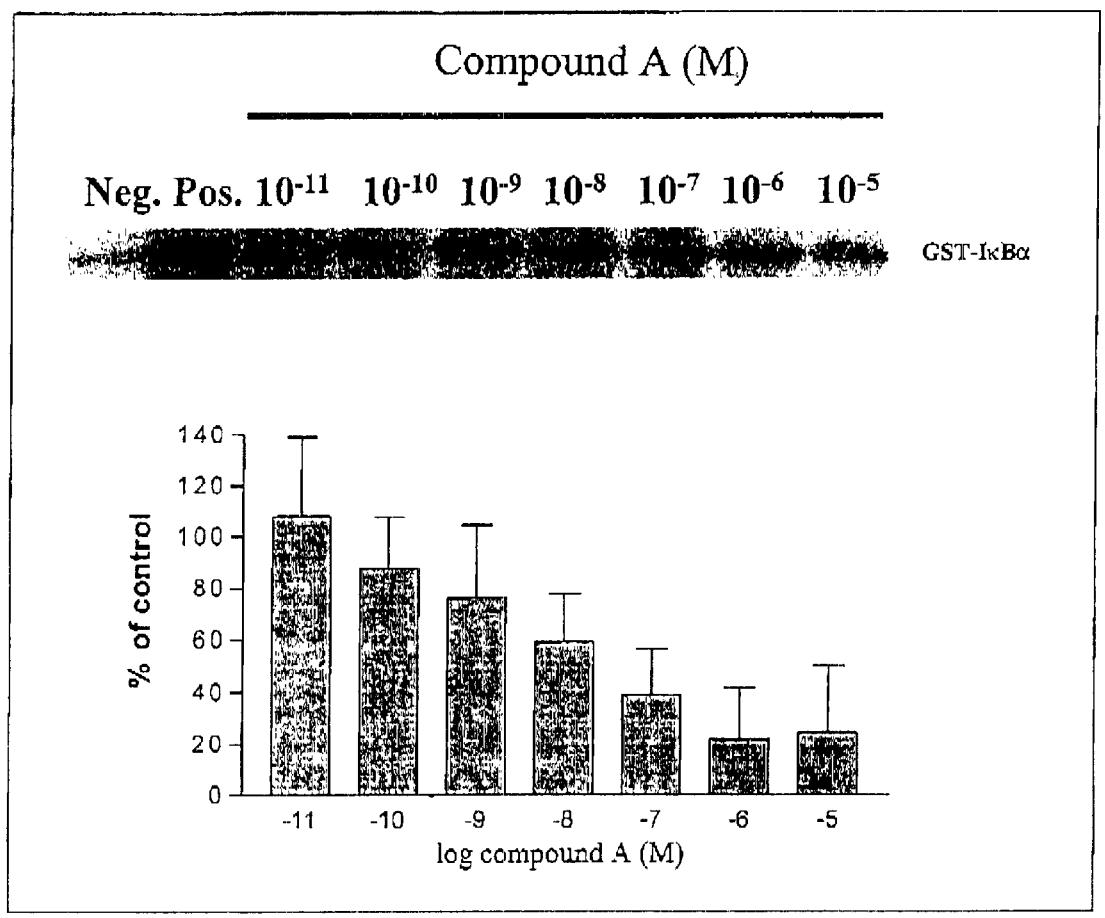
FIG. 4 shows that compound A inhibits the LPS-induced IKKβ activity in vitro. THP-1 cells were starved over night in 2% FCS followed by incubation with 1 μg/ml LPS for 12 min. The lysed cells were subjected to immunoprecipitation using the IKKα/β antibody. Compound A was added at different concentrations to the activated, isolated IKKβ and incubated for 30 min. at 30° C. The kinase reaction was then performed using 2.5 μg GST-IκBα as a substrate for 30 min. at 3° C. The proteins were resolved on a SDS-PAGE and the phosphorylation of GST-IκBα was quantified using the ImageQuant software. One representative gel picture is presented while the plot shows the mean IKKβ activity from 4 independent experiments ±SD. The values from the negative controls (myricetin-treated kinase) were subtracted from all raw data. Data are expressed as percent of the positive control (DMSO-treated kinase).

IKK activity: Upon cellular activation by extracellular stimuli, IκB proteins are phosphorylated by a large IκB kinase complex. An in vitro IKK activity assay was established to evaluate a possible effect of compound A on the IKK activity. The THP-1 cells were stimulated with 1 μg/ml LPS for 12 min, and then the cells were lysed and immunoprecipitated by an IKK antibody. The purified IKK was then pretreated with various concentrations of compound A ranging from $10^{-11}$ to $10^{-5}$ M for 30 min. prior to the IKK activity assay (FIG. 4). A "chemical zero-point" was introduced by treating the LPS-activated IKK with the IKKβ inhibitor myricetin (20 μM) (S. H. Tsai et al., supra) to overcome the problem with a prestimulated kinase. A clear dose-response was observed as illustrated by the decrease of GST-IκBα phosphorylation in the compound A-treated samples. Four independent experiments were performed and the results are summarised on the plot (FIG. 4). The $IC_{50}$ values range from 0.9 nM to 70 nM with a mean $IC_{50}$ value of 8 nM.

Example 4

Different NF-κB Activities in Different Cell Lines

Methods

The NF-κB-luciferase reporter plasmid (pBIIX) and pRL-TK control vector described in Example 1 were used for the luciferase assay, Transfection assays; The THP-1 cells were transiently transfected during the log phase of growth using the DEAE-dextran transfection procedure described in Example 1.

The Colo-320 cells were seeded with a density of $5 \times 10^4$ cells/cm$^2$ in 6-well plates (NUNC). The following day, the cells were co-transfected with construct DNA and pRL-TK using FuGene Transfection Reagent (Boehringer Mannheim). A mixture of 5 µl Fugene and 95 µl serum free medium (per well) was prepared and incubated for 5 min at room temperature. Then, the mixture was transferred to a mixture of construct DNA (2.5 µg per well) and pRL-TK vector (0.25 µg per well), gently mixed, incubated for 15 min at room temperature and added to the cells. The cells were treated at 37° C. with compound A ($10^{-12}$–$10^{-5}$ M) or DMSO for 24 h before stimulation with TNF-α (50 ng/ml) for 6 h.

The HT-1080 cells were seeded at a density of $3 \times 10^4$ cells/cm$^2$ in 6 well-plates. The following day, the cells were co-transfected with construct DNA and pRL-TK vector using FuGene Transfection Reagent. A mixture of 10 µl Fugene and 90 µl serum free medium (per well) was prepared and Incubated for 5 min at room temperature. Then, this mixture was transferred to a mixture of construct DNA (1.25 µg per well) and pRL-TK vector (0.25 µg per well), gently mixed, incubated for 15 min at room temperature and added to the cells. The cells were treated at 37° C. with compound A ($10^{-12}$–$10^{-5}$ M) or DMSO for 24 h before stimulation with TNF-α (50 ng/ml) for 6 h.

The PC-3 cells were seeded at a density of $3 \times 10^4$ cells/cm$^2$ in 6 well-plates. The following day, the cells were co-transfected with construct DNA and pRL-TK vector using DOTAP liposomal transfection reagent (Boehringer Mannheim). The construct DNA (4.0 µg per well), the pRL-TK vector (1.0 µg per well), DOTAP (16.7 µl per well) and dH$_2$O (total volume 100 µl per well) were carefully mixed and incubated for 15 min at 37° C. A growth medium without serum (900 µl per well) was added and the transfection mixture (1 ml per well) was added to the cells. After 4 h at 37° C., a growth medium with 20% FBS (1 ml per well) was added. The cells were treated at 37° C. with compound A ($10^{-12}$–$10^{-5}$ M) or DMSO for 24 h before stimulation with TNF-α (50 ng/ml) for 6 h.

The cell lysate was assayed for luciferase activity using the Dual luciferase kit as described by the manufacturer (Promega). All transfections were performed in triplicate. Firefly luciferase activity was corrected for differences in transfection efficiency by normalizing it to the measured *Renilla luciferase* activity.

Results

Figure 5:
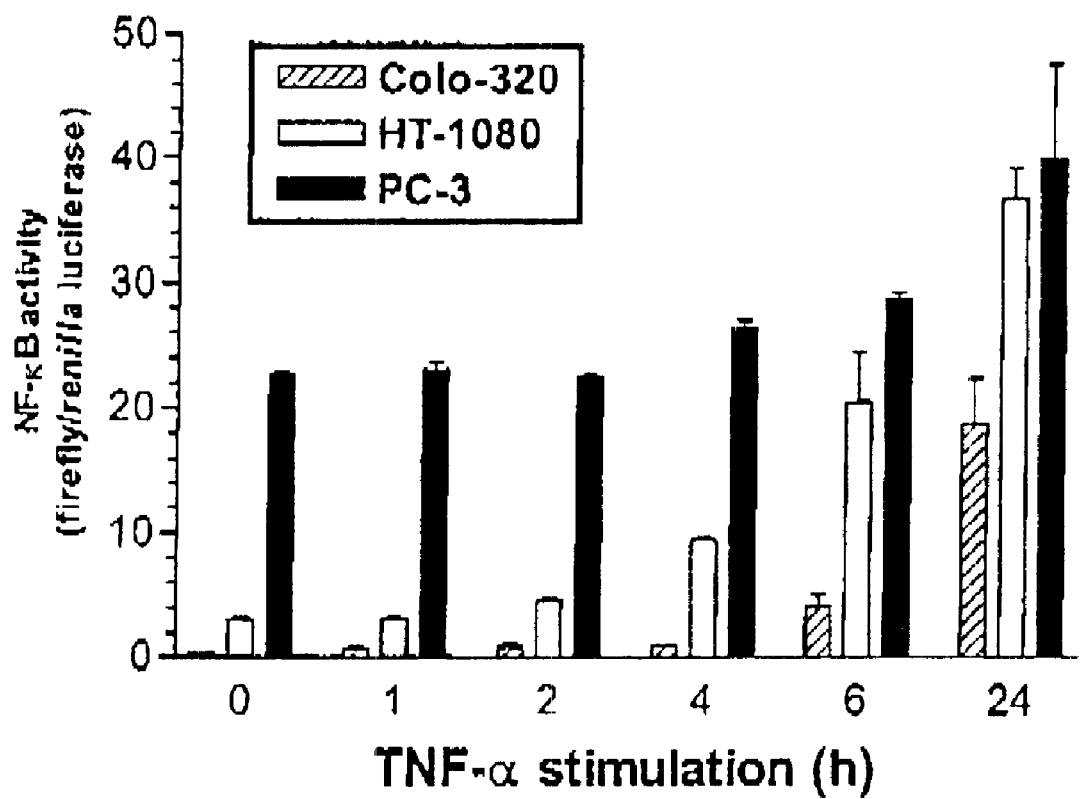
FIG. 5 shows that THP-1, PC-3, Colo-320 and HT-1080 differ for NF-κB. The cells were seeded at a density of $5×10^4$ cells/cm$^2$ (Colo-320) or $3×10^4$ cells/cm$^2$ (HT-1080, PC-3) in 6 well-plates. The following day, the cells were co-transfected with a NF-κB-luciferase reporter plasmid (firefly luciferase) and *Renilla luciferase* plasmid (*Renilla luciferase*). Then, the cells were treated with TNF-α (50 ng/ml) for 0–24 h, lysed and finally, analyzed for luciferase activity. The results were normalized with respect to transfection efficiency, and thus the NF-κB activity is expressed as firefly luciferase activity/*Renilla luciferase* activity. The bars represent the mean (+/−SD) of one representative experiment out of three performed in triplicate. A. Colo-320 cells, B. HT-1080 cells, C. PC-3 cells.

Luciferase activity: Afterwards, the cells were treated for 0–24 h with or without 50 ng/ml TNF-α and the NF-κB activity was evaluated in the luciferase assay (FIG. 5B). Strikingly, the basal level of NF-κB activity measured with the luciferase assay was very high in the PC-3 cells compared with the two other cell lines. Treatment of the HT-1080 cells and Colo-320 with TNF-α increased the transcriptional activity of NF-κB after 4 and 6 h of treatment (FIG. 5). Prolonged TNF-α-treatment for up to 24 h increased the NF-κB activity to approximately 12 and 46 fold compare to the control. In contrast, when the PC-3 cells were stimulated with TNF-α, only a small effect on the NF-κB activity was observed, even after long-term treatment (24 h).

Example 5

Effect of Compound A on Cell Proliferation in Different Cell Lines as Well as in vivo Effect in Nude Mice Methods DNA synthesis: NYH SCLC, HT-1080, Colo-320, PC-3 and H460 cells ($7.5 \times 10^3$ cells/ml) were seeded in tissue culture vessels and the test compound were added 2 h after plating. Following an incubation for 144 h tritiated thymidine (5 CI/mmol, Amersham Pharmacia Biotech) was added to the culture at the concentration of 1 µCi/ml, and the cells were incubated for additional 4 h. The incorporated thymidine was measured with a β-counter. Each compound concentration was tested in triplicate.

NF-κB activity was measured by the luciferase assay described in Example 1.

Animal Models

All of the animal experiments were conducted according to the guidelines and ethical standards of the Danish Committee for Animal Experiments. Female NMRI nu/nu mice 6 weeks of age were purchased from M&B (Ry, Denmark). The mice were allowed an acclimatisation period of 1–3 weeks before start of the experiments. The nude mice were housed in Scantainers under semi-sterile conditions and all handling of mice was performed in a laminar flow bench.

NYH Xenografts. NMRI nu/nu mice were injected with $1 \times 10^7$ cells in 0.2 ml media s.c. in both flanks and tumour growth was measured twice weekly. The tumour area was used as expression of the tumour size and was calculated from two perpendicular diameters measured with a digital caliper. Compound A was given for fourteen consecutive days by oral gavage from day 4–6 when the tumour size was 24–30 mm$^2$. Each treatment group consisted of 10 mice.

HT 1080 Xenografts. NMRI nu/nu mice were injected with $2 \times 10^6$ cells in 0.2 ml media s.c. in each flank and tumour size was measured as described for the NYH model. Compound A was given for fourteen days by oral gavage from day 4 when the tumour size was 22–24 mm$^2$. Each treatment group consisted of 10 mice.

PC-3 Xenografts. NMRI nu/nu mice were injected with $1 \times 10^6$ cells in 0.2 ml media s.c. in each flank and tumour size was measured as mentioned above. Compound A was given for four weeks by oral gavage from day 14 when the tumour size was about 12 mm$^2$. Each treatment group consisted of 10 mice.

Colo-320 DM, NMRI nu/nu mice were injected with $5 \times 10^6$ cells in 0.2 ml media s.c. in each flank and tumour size was measured as mentioned above. Compound A was given for three weeks by oral gavage from day 8 when the tumour size was about 20 mm$^2$. Each treatment group consisted of 10 mice.

Statistical Methods In the animal models, tumour sizes were expressed by the mean of the trends in each treatment group. The trend is the linear increment or tumour size, where tumour size is the square root of the (mean) area of the tumour(s). Comparison with controls was expressed as T/C % and calculated as follows:

$[A/B-1]*100$ where

A=(overall mean tumour size at baseline+mean trend of treatment*intended days of treatment)

B=(overall mean tumour size at baseline+mean trend of control*intended days of treatment)

Overall mean tumour size at baseline=pooling all treatments this is the mean of all baseline values. For each mouse the baseline value is calculated as the square root of the (mean) area of the tumour(s).

Significance was tested with the Bonferroni correction. This correction is a method for adjusting (lowering) the significance level so the overall finding of one significant difference due to chance is around 5 percent.

Results

The results are shown in Table 1 below.

TABLE 1

| Cell line | DNA synthesis ($IC_{50}$ nM)[a] | NF-κB activity ($IC_{50}$ nM)[b] | In vivo xenografts in nude mice (50 mg/kg) | |
|---|---|---|---|---|
| | | | T/C (%)[c] | p-value[d] |
| NYH SCLC | 0.64 ± 0.06 | — | −100 | <0.05 |
| HT-1080 | 5.6 ± 0.3 | 2480 ± 775 | −77 | <0.05 |
| Colo-320 | 5.4 ± 0.1 | 84 ± 33 | −50 | <0.01 |
| PC-3 | 5.6 ± 0.3 | no inhibition | −5 | n. s. |

[a]Incorporation of tritiated thymidine. Results are expressed as the mean $IC_{50}$ concentration ± SD of two to four experiments.
[b]NF-κB-dependent luciferase activity. Results are expressed as the mean $IC_{50}$ concentration ± SD of two to four experiments.
[c]T/C %: Median tumour area in the treated group/median tumour area in the vehicle group after 14 days of treatment (from day 14 to day 28).
[d]Statistics by the Bonferroni correction. n. s. not significant.

The results show a tendency to correlate between the NF-κS activity in vitro and the in vivo effect of compound A. They further show that different cell lines have different sensitivities to the active compound.

Example 6

Effect of Different Cyanoguanidines on IKK Activity, NF-κB Activity in THP-1 Cells, DNA Synthesis in NYH SCLC Cells and in Nude Mice with NYH SCLC Tumours IKK activity was determined by means of the assay described in Example 3. NYH cell proliferation was determined by measuring the amount of tritiated thymidine incorporated in the cells as described in Example 5.

The results are shown in Table 2 below.

TABLE 2

| Compound | IKK activity in vitro ($IC_{50}$ nM)[a] | NYH proliferation in vitro ($IC_{50}$ nM)[b] | NYH tumor growth in vivo (T/C in %)[c] |
|---|---|---|---|
| B | 6.5 ± 5 | 0.58 ± 0.03 | −84.5 |
| A | 8.0 ± 2.2 | 0.64 ± 0.06 | −44 |
| C | 22 ± 2.4 | 567 ± 127 | — |
| D | >$10^{-5}$ (M) | 573 ± 219 | — |
| E | >$10^{-5}$ (M) | 597 ± 42 | −17.1 |

[a]GST-IκB was phosphorylated by activated IKK pretreated with the compound
[b]Incorporation of tritiated thymidine in NYH SCLC cells
[c]T/C %: Median tumour area in the treated group/median tumour area in the vehicle group after 14 days of treatment with 20 mg/kg (from day 14 to day 28).

These results show a correlation between the in vitro and in vivo effect of different cyanoguanidines, compound B and compound A being potent compounds, while compounds C, D and E have little effect in vitro and no effect in vitro.

What is claimed is:

1. A method of modulating the level of activated NF-κB in cells, the method comprising contacting cells with a compound of general formula I

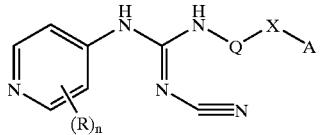

wherein
n is 0, 1 or 2;
each R independently represents halogen, trifluoromethyl, hydroxy, $C_{1-4}$ alkyl, $C_{1-4}$ alkoxy, $C_{1-4}$ alkoxycarbonyl, nitro, cyano, amino, sulfo or carboxy groups;
Q is a straight or branched, saturated or unsaturated $C_{4-20}$ divalent hydrocarbon radical;
X is a bond, O, S, amino, carbonyl, carbonylamino, aminocarbonyl, oxycarbonyloxy, oxycarbonyl, carbonyloxy, aminocarbonyloxy, aminothiocarbonyloxy, oxycarbonylamino or oxythiocarbonylamino;
A is di-($C_{1-4}$ alkoxy)phosphinoyloxy, $C_{1-4}$ alkoxycarbonyl, $C_{1-4}$ alkoxycarbonylamino, a saturated or unsaturated $C_{3-12}$ carbocyclic ring or $C_{3-12}$ heterocarbocyclic ring optionally substituted with one or more $R_1$; $R_1$ being independently selected from the group consisting of halogen, trifluoromethyl, hydroxy, $C_{1-4}$ alkyl, $C_{1-4}$ alkoxy, $C_{1-4}$ alkoxycarbonyl, nitro, cyano, amino, carboxy, sulfo, carboxamido, sulfamoyl or $C_{1-4}$ hydroxyalkyl;
or a pharmaceutically acceptable salt, N-oxide or N-substituted prodrug thereof in an amount effective to modulate the activity of IKK.

2. A method according to claim 1 wherein A is phenyl optionally substituted by one or more substituents selected from the group consisting of halogen, trifluoromethyl, hydroxy, $C_{1-4}$ alkyl, $C_{1-4}$ alkoxycarbonyl, nitro, cyano, amino, carboxy, sulfo, carboxamido, sulfamoyl or $C_{1-4}$ hydroxyalkyl.

3. A method according to claim 1 wherein X is O.

4. A method according to claim 1 wherein Q is a $C_{4-12}$ divalent hydrocarbon radical.

5. A method according to claim 1 wherein n is 0.

6. A method according to claim 1 wherein R is $C_{1-4}$ alkoxy, and n is 1.

7. A method according to claim 1 wherein X is a bond and A is di-($C_{1-4}$ alkoxy)phosphinoyloxy.

8. A method according claim 1 wherein the compound is selected from the group of compounds consisting of N-(6-(4-chlorophenoxy)hexyl)-N'-cyano-N"-(4-pyridyl) guanidine;

N-cyano-N'-(9-diethylphosphionyloxynonyl)-N"-(4-pyridyl)guanidine;

N-(6-(4-chlorophenoxy)hexyl-N"-cyano-N"-(2-methoxy-5-pyridyl) guanidine; or

N-(tert-butoxycarbonylamino-dodecyl)-N'-cyano-N"-(4-pyridyl)guanidine.

9. A method according to any of claims 1–8 wherein the cells are neoplastic cells.

10. A method according to any of claims 1–8 wherein the cells are cancer cells.

11. A method according to any of claims 1–8 wherein the cells are cancer cells resistant to chemotherapy and/or ionising radiation.

12. A method according to claim 1, wherein the level of activated NF-κB is reduced.

13. A method according to claim 1, wherein IKK or a subunit thereof is inhibited.

14. A method according to claim 13, wherein IKKβ is inhibited.

15. A method of reducing the anti-apoptotic effect of NF-κB in cells, the method comprising contacting cells with a compound of general formula I

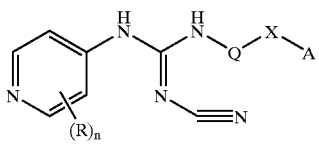

wherein
- n is 0, 1 or 2;
- each R independently represents halogen, trifluoromethyl, hydroxy, $C_{1-4}$ alkyl, $C_{1-4}$ alkoxy, $C_{1-4}$ alkoxycarbonyl, nitro, cyano, amino, sulfo or carboxy groups;
- Q is a straight or branched, saturated or unsaturated $C_{4-20}$ divalent hydrocarbon radical;
- X is a bond, O, S, amino, carbonyl, carbonylamino, aminocarbonyl, oxycarbonyloxy, oxycarbonyl, carbonyloxy, aminocarbonyloxy, aminothiocarbonyloxy, oxycarbonylamino or oxythiocarbonylamino;
- A is di-($C_{1-4}$ alkoxy)phosphinoyloxy, $C_{1-4}$ alkoxycarbonyl, $C_{1-4}$ alkoxycarbonylamino, saturated or unsaturated $C_{3-12}$ carbocyclic ring or $C_{3-12}$ heterocarbocyclic ring optionally substituted with one or more $R_1$; $R_1$ being independently selected from the group consisting of halogen, trifluoromethyl, hydroxy, $C_{1-4}$ alkyl, $C_{1-4}$ alkoxy, $C_{1-4}$ alkoxycarbonyl, nitro, cyano, amino, carboxy, sulfo, carboxamido, sulfamoyl or $C_{1-4}$ hydroxyalkyl;
- or a pharmaceutically acceptable salt, N-oxide or N-substituted prodrug thereof in an amount effective to inhibit IKK.

16. A method according to claim 15 wherein A is phenyl optionally substituted by one or more substituents selected from the group consisting of halogen, trifluoromethyl, hydroxy, $C_{1-4}$ alkyl, $C_{1-4}$ alkoxycarbonyl, nitro, cyano, amino, carboxy, sulfo, carboxamido, sulfamoyl or $C_{1-4}$ hydroxyalkyl.

17. A method according to claim 15 wherein X is O.

18. A method according to claim 15 wherein Q is a $C_{4-12}$ divalent hydrocarbon radical.

19. A method according to claim 15 wherein n is 0.

20. A method according to claim 15 wherein R is $C_{1-4}$ alkoxy, and n is 1.

21. A method according to claim 15 wherein X is a bond and A is di-($C_{1-4}$ alkoxy)phosphinoyloxy.

22. A method according claim 15 wherein the compound is selected from the group consisting of
- N-(6-(4-chlorophenoxy)hexyl)-N'-cyano-N''-(4-pyridyl) guanidine;
- N-cyano-N'-(9-diethylphosphionyloxynonyl)-N''-(4-pyridyl)guanidine;
- N-(6-(4-chlorophenoxy)hexyl-N''-cyano-N''-(2-methoxy-5-pyridyl)guanidine; or
- N-(tert-butoxycarbonylamino-dodecyl)-N'-cyano-N'-(4-pyridyl)guanidine.

23. A method according to any of claims 15–22 wherein the cells are neoplastic cells.

24. A method according to any of claims 15–22 wherein the cells are cancer cells.

25. A method according to any of claims 15–22 wherein the cells are cancer cells resistant to chemotherapy and/or ionising radiation.

26. A method accordingt to claim 15 for inhibiting IKKβ.

27. A method of inhibiting IKK, the method comprising contacting cells with a compound of general formula I

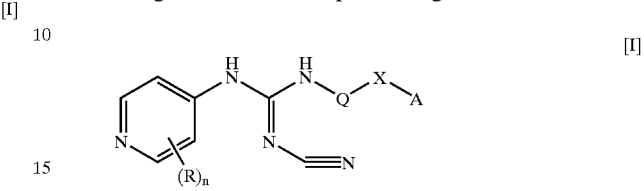

wherein
- n is 0, 1 or 2;
- each R independently represents halogen, trifluoromethyl, hydroxy, $C_{1-4}$ alkyl, $C_{1-4}$ alkoxy, $C_{1-4}$ alkoxycarbonyl, nitro, cyano, amino, sulfo or carboxy groups;
- Q is a straight or branched, saturated or unsaturated $C_{4-20}$ divalent hydrocarbon radical;
- X is a bond, O, S, amino, carbonyl, carbonylamino, aminocarbonyl, oxycarbonyloxy, oxycarbonyl, carbonyloxy, aminocarbonyloxy, aminothiocarbonyloxy, oxycarbonylamino or oxythiocarbonylamino;
- A is di-($C_{1-4}$ alkoxy)phosphinoyloxy, $C_{1-4}$ alkoxycarbonyl, $C_{1-4}$ alkoxycarbonylamino, saturated or unsaturated $C_{3-12}$ carbocyclic ring or $C_{3-12}$ heterocarbocyclic ring optionally substituted with one or more $R_1$; $R_1$ being independently selected from the group consisting of halogen, trifluoromethyl, hydroxy, $C_{1-4}$ alkyl, $C_{1-4}$ alkoxy, $C_{1-4}$ alkoxycarbonyl, nitro, cyano, amino, carboxy, sulfo, carboxamido, sulfamoyl or $C_{1-4}$ hydroxyalkyl;
- or a pharmaceutically acceptable salt, N-oxide or N-substituted prodrug thereof in an amount effective to inhibit IKK.

28. A method according to claim 27 wherein A is phenyl optionally substituted by one or more substituents selected from the group consisting of halogen, trifluoromethyl, hydroxy, $C_{1-4}$ alkyl, $C_{1-4}$ alkoxycarbonyl, nitro, cyano, amino, carboxy, sulfo, carboxamido, sulfamoyl or $C_{1-4}$ hydroxyalkyl.

29. A method according to claim 27 wherein X is O.

30. A method according to claim 27 wherein Q is a $C_{4-12}$ divalent hydrocarbon radical.

31. A method according to claim 27 wherein n is 0.

32. A method according to claim 27 wherein R is $C_{1-4}$ alkoxy, and n is 1.

33. A method according to claim 27 wherein X is a bond and A is di-($C_{1-4}$ alkoxy)phosphinoyloxy.

34. A method according claim 27 wherein the compound is selected from the group consisting of
- N-(6-(4-chlorophenoxy)hexyl)-N'-cyano-N''-(4-pyridyl) guanidine;
- N-cyano-N'-(9-diethylphosphionyloxynonyl)-N''-4-pyridyl guanidine;
- N-(6-(4-chlorophenoxy)hexyl-N''-cyano-N''-(2-methoxy-5-pyridyl) guanidine; or N-(tert-butoxycarbonylamino-dodecyl)-N'-cyano-N"-(4-pyridyl)guanidine.

35. A method according to any of claims 27–34 wherein the cells are neoplastic cells.

36. A method according to any of claims 27–34 wherein the cells are cancer cells.

37. A method according to any of claims 27–34 wherein the cells are cancer cells resistant to chemotherapy and/or ionising radiation.

38. A method according to claim 27, wherein IKKβ is inhibited.

* * * * *